United States Patent [19]

Pawliszyn

[11] Patent Number: 4,940,333

[45] Date of Patent: Jul. 10, 1990

[54] METHOD AND APPARATUS FOR DETECTING UNIVERSALLY AND SELECTIVELY CONCENTRATION GRADIENTS, AND FOR DEFLECTING A LIGHT BEAM IN A CONTROLLED FASHION

[75] Inventor: Janusz B. Pawliszyn, Logan, Utah

[73] Assignee: Anthony R. Torres, Salt Lake City, Utah

[21] Appl. No.: 271,034

[22] Filed: Nov. 14, 1988

Related U.S. Application Data

[62] Division of Ser. No. 948,247, Dec. 31, 1986, Pat. No. 4,784,494.

[51] Int. Cl.⁵ ............................................. G01N 21/41
[52] U.S. Cl. ..................................... 356/432; 356/128; 350/353
[58] Field of Search ........... 356/128, 344, 432, 432 T; 350/413, 353, 354

[56] References Cited

U.S. PATENT DOCUMENTS

| | | | |
|---|---|---|---|
| 3,812,482 | 5/1974 | Clark | 356/39 |
| 3,859,103 | 1/1975 | Yoshiyagawa et al. | 350/413 |
| 4,468,136 | 8/1984 | Murhpy et al. | 356/128 |
| 4,547,071 | 10/1985 | Teitelbaum | 356/344 |
| 4,585,301 | 4/1986 | Bialkowski | 350/354 |
| 4,591,272 | 5/1986 | Morris et al. | 356/432 |
| 4,641,965 | 2/1987 | Harmer | 356/128 |
| 4,666,308 | 5/1987 | Williams | 356/432 |
| 4,681,437 | 7/1987 | Owen et al. | 356/128 |
| 4,738,502 | 4/1988 | Mikami et al. | 350/353 |

FOREIGN PATENT DOCUMENTS

| | | | |
|---|---|---|---|
| 54915 | 4/1982 | Japan | 350/413 |
| 262637 | 11/1986 | Japan | 356/128 |

OTHER PUBLICATIONS

Hilbert, Robert S., "Gradient Index is Growing", *Photonics Spectra*, (Dec. 1982), pp. 59-62.

W. Herrmann and D. W. Pohl, Trace Analysis on Gases by Laser-Induced Schlieren Technique, IBM Technical Disclosure, vol. 21, No. 10, Mar. 1979.

*Primary Examiner*—Richard A. Rosenberger
*Attorney, Agent, or Firm*—Mallinckrodt & Mallinckrodt

[57] ABSTRACT

Concentration gradients in samples to be evaluated are detected by measuring the deflection of a probe light beam passed through the sample using the principals of Schlieren optics. Specific chemical compounds in a sample can be detected and identified by supplying excitation energy to the sample where such energy is selected to be absorbed by the chemical compound to be specifically identified and not by other compounds in the sample. The absorption of the excitation energy by the absorbing compound produces a temperature gradient within the sample which causes deflection of the probe light beam and signals representative of such deflection may be separated from signals representative of deflections caused by other refractive index gradient present in the sample. A light emitting diode may be used to generate the probe light beam. Rather than detecting movement of the probe light beam caused by an unknown gradient, by passing the probe light beam through a known gradient, with or without excitation energy present, the light beam can be deflected in a controlled manner.

15 Claims, 3 Drawing Sheets

FIG. 14
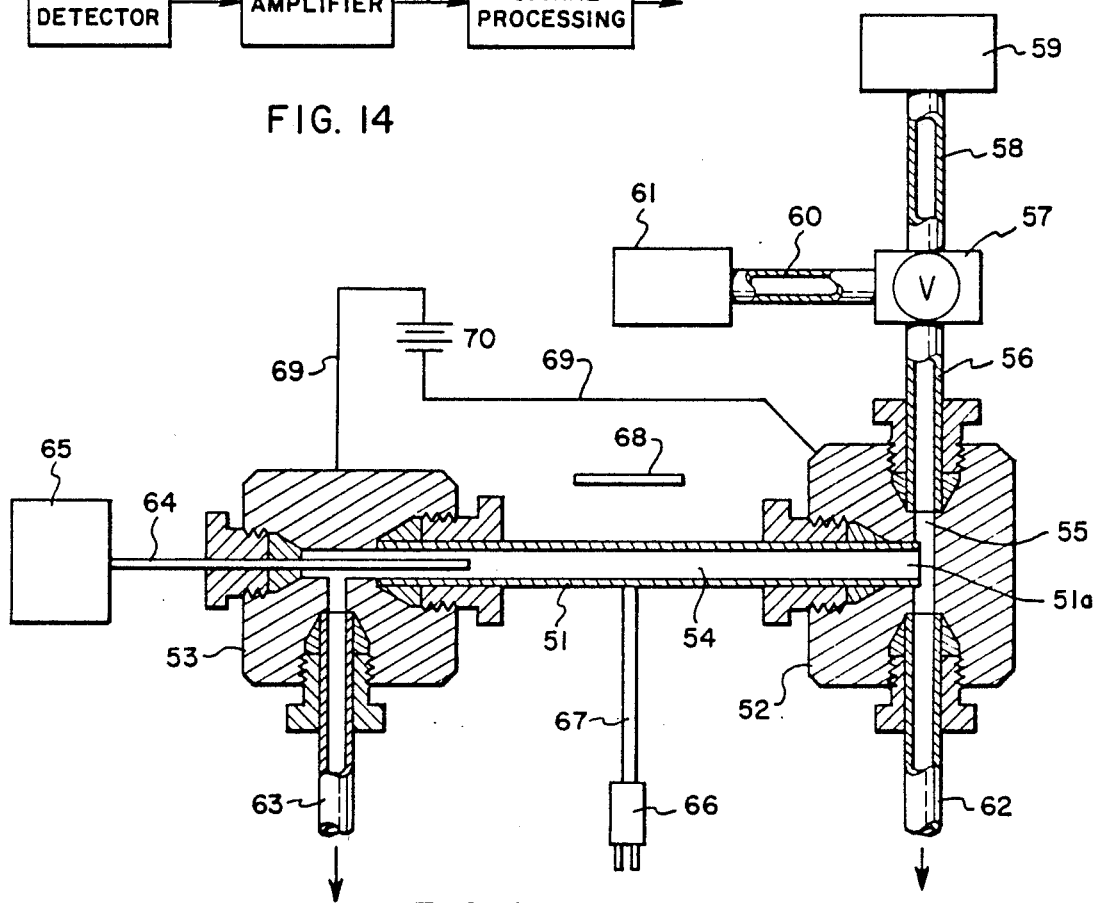
FIG. 9
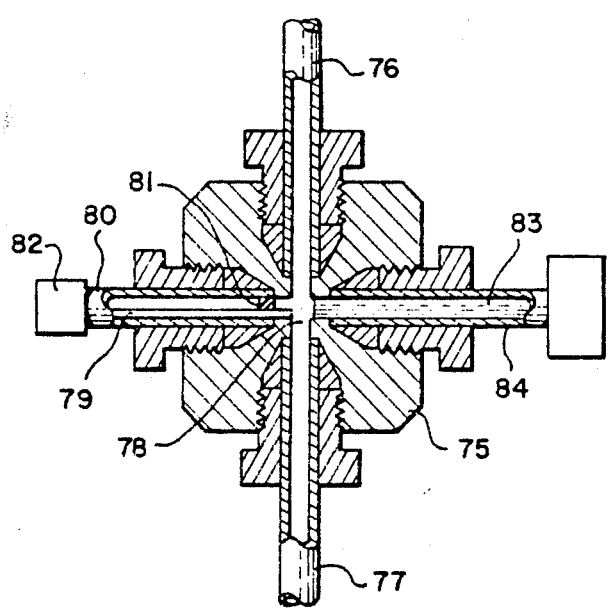
FIG. 10
FIG. 12
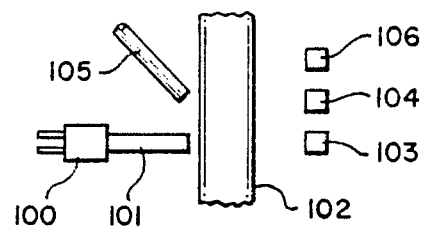
FIG. 13

METHOD AND APPARATUS FOR DETECTING UNIVERSALLY AND SELECTIVELY CONCENTRATION GRADIENTS, AND FOR DEFLECTING A LIGHT BEAM IN A CONTROLLED FASHION

BACKGROUND OF THE INVENTION

1. Field:

The invention is in the field of detection methods and apparatus based on Schlieren optics.

2. State of the Art:

It has been known for some time that a refractive index gradient such as produced by a concentration gradient in a fluid such as gas, liquid or supercritical fluid, will cause deflection of light passing through this gradient. The optical method of observing and measuring the deflection of light caused by refractive index gradient fields is generally referred to as Schlieren optics. In most past applications, Schlieren images resulting from light deflections have been recorded on photographic plates and the plates then analyzed for light intensity distribution using densitometers. Recently, evaluation of the photographic images has been done by computer. These methods are useful in studying plasmas where very complicated toroidal and parabolic shapes are generated.

U.S. Pat. No. 4,547,071 discloses a sensor for measuring density gradients in a nonhomogenious fluid sample using Schlieren optics. In such sensor, a laser light beam is directed through a sample chamber and is moved along said chamber. A quadrant light position sensor located on the opposite side of the chamber detects the deflection of the laser light beam as it is moved through the sample. The amount of deflection indicates the density gradient at any point in the sample. Rather than moving the laser beam along the sample chamber, the beam can be held constant and the sample moved within the chamber.

While the detector of U.S. Pat. No. 4,547,071 will give an indication of the density gradients in a sample, the detector measures all density gradients equally and is not specific for any particular chemical substance. It is often desireable to be able to specifically identify a particular chemical substance. Further, laser light is not as positionally and intensity stable as is necessary for high sensitivity applications.

A current development in the field of high performance liquid chromatography is the open tubular capillary column which provide ultra high efficiency separation of sample components. This method requires very small sample volumes. However, there are currently no simple detectors available which can detect the small volumes of the separated components produced by these columns. Similar problems exist in the field of capillary zone electrophoresis where small volume samples are used. There is a need for a simple, easily used detector that can detect and identify the individual separated components of a sample of very small volume such as smaller than 100 nanoliters.

SUMMARY OF THE INVENTION

According to the invention, a detector which measures concentration gradients within a sample in a sample chamber can also selectively identify specific chemical components that may be present in the sample. A detector of the invention includes a sample chamber, a light source adapted to pass a probe beam of light through the sample chamber, means for detecting the position of the probe beam of light after passing through and leaving the sample chamber, and means for periodically supplying excitation energy to the sample chamber adapted to be absorbed by preselected chemical compounds if present in the chamber. In this way, if the preselected chemical compound is present, it will absorb the excitation energy and create a temperature gradient through photothermal process in the sample that substantially corresponds to the concentration gradient of that chemical in the sample. This temperature gradient will form refractive index gradient and therefore it will also be detected by the probe light beam passing through the sample chamber. Thus, not only can all of the concentration gradients of the sample be detected, but also, by supplying the excitation energy to the sample, the presence or absence of the predetermined chemical compound which absorbs the excitation energy can be positively detected and separated from the other compounds detected.

A preferred light source for use with the invention is a light emitting diode (LED) which unexpectedly has been found superior in most applications to a laser for generating the probe light beam which is passed through the sample chamber. The probe light beam generated by an LED has been found to be more positionally and intensity stable than a light beam generated by a laser and allows more sensitivity in gradient measurements. Increased sensitivity results in detection of lower concentration components in a sample.

Where gradients in a sample are too small to be successfully detected by merely flowing the sample through a detector of the invention, or where it is desired to determine whether or not a particular chemical compound is present in a homogenious sample, and if present, to determine the concentration thereof in the sample, concentration gradients within the sample may be created by electrochemical means, i.e. by providing an electrode with electrical charge thereon to create a desired concentration gradient adjacent the electrode which can be detected and measured as indicated above. Selective detection along such induced gradient can be accomplished by supplying excitation energy to the sample adjacent to the electrode.

Another method that may be used to create a concentration gradient that can be detected by the invention is by means of flow injection analysis. Thus, if a homogenious sample is to be evaluated, it is possible to inject small volumes of the sample in a stream of solvent flowing through the detector thereby creating a concentration gradient as the sample flowing through the sample chamber changes from solvent to sample and back to solvent.

The invention includes the method of identifying the presence of a preselected chemical compound in a sample comprising the steps of moving the sample through a sample chamber, passing a probe beam of light through the sample chamber, selecting an excitation energy so that such energy will be absorbed by the chemical compounds preselected to be identified but not by other chemical compounds in the sample, supplying the excitation energy to the sample so that such excitation energy will be absorbed by the preselected chemical compound if present in the sample thereby causing the creation of a temperature gradient through photothermal process in the sample, and measuring the deflection of the probe beam of light passing through the sample caused by the presence of concentration gradients within the sample, and the additional deflection of the probe light beam caused by the presence of the temperature gradient.

THE DRAWINGS

The best modes presently contemplated for carrying out the invention are shown in the accompanying drawings in which:

FIG. 1 is a schematic representation of a light beam passing through a gradient;

FIG. 2, a schematic representation of a light beam passing through a sample chamber, showing the deflection angle produced by the presence of a refractive index gradient in the chamber;

FIG. 3, a second schematic representation of a light beam passing through a sample chamber with a concentration gradient;

FIG. 4, a schematic representation similar to that of FIG. 3 but showing an additional temperature gradient in the sample chamber;

FIG. 5, a schematic representation of a detector of the invention;

FIG. 6, an enlarged view of the light beam position detector of FIG. 5;

FIG. 7, a comparison of the concentration profile of a sample in a detector of the invention and various output curves produced by the detector;

FIG. 8, a circuit diagram of a position detector suitable for use with the invention;

FIG. 9, a schematic representation of a second embodiment of a detector of the invention used as a capillary zone electrophoresis device;

FIG. 10, a schematic representation of a third embodiment of a detector of the invention;

FIG. 11, a circuit diagram of a position detector suitable for use with the detector of FIG. 10;

FIG. 12, a fragmentary schematic representation of a sample chamber with an electrode therein;

FIG. 13, a fragmentary schematic representation of an embodiment of the invention used to direct a light beam in a desired manner; and FIG. 14, a block diagram showing an embodiment of the processing circuitry of the invention.

DETAILED DESCRIPTION OF THE ILLUSTRATED EMBODIMENTS

Figure 1:
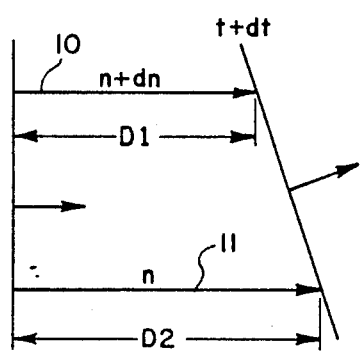

It is well known that light passing through a refractive index gradient in a solution is deflected. The physical reason for light deflection when passing through this gradient lies in the relationship between the refractive index and light propagation velocity. Different parts of the light advance to a different degree with time, which generates the phase shift. Thus, as shown in FIG. 1, during a given time period t+dt, light at the top of a light beam indicated by arrow 10 which is passing through a solution with a refractive index of n+dn will travel a distance of D1. The light at the bottom of the light beam indicated by arrow 11 which is passing through a solution with a refractive index of n will travel a distance D2. This results in a tilt of the light wavefront and since light travels perpendicular to the wavefront, the light beam is tilted as illustrated. In FIG. 1, D2 is greater than D1 resulting in an upward tilt, but depending upon the values of n and n+dn, the tilt could be downward.

The light path through the refractive index gradient can be calculated by using the Fermat principle that the light path through the medium is such that the time necessary for its traversal is minimum. The relationship between the angle of deflection, $\theta$, and the refractive index gradient normal to the light propagation dn/dx and path length through this gradient, D, can be written as $$\tan\theta = \sinh(D/n)(dn/dx) = (D/n)(dn/dx) + (dn/dx)^3(D^3/n^3 3!) + (dn/dx)^5(D^5/n^5 5!) + \ldots$$

where n is the refractive index of the medium. In situations where the sensors of the invention will be used, D and $\theta$ are small. We can then approximate:

$$\theta = (D/n)(dn/dx)$$

Figure 2:
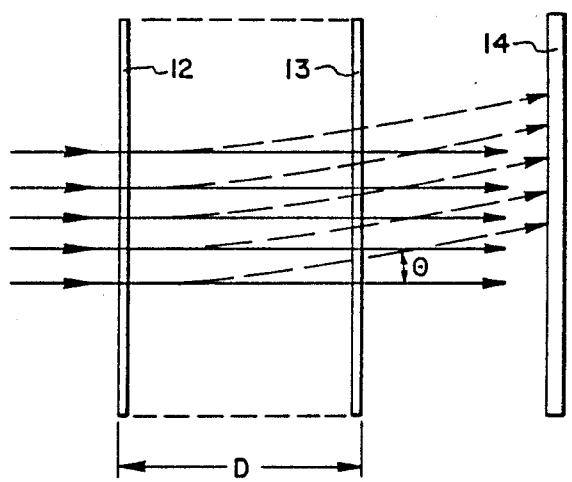

FIG. 2 illustrates the detection principle behind this method. With a nonuniform distribution of a solute in the sample chamber shown schematically between sample chamber walls 12 and 13 giving a sample chamber distance D, a concentration gradient is established. This gradient forms the corresponding refractive index gradient dn/dx=(dn/dc)(dc/dx), which then tilts or deflects the propagating light beam by angle $\theta = (D/n)(dn/dc)(dc/dx)$. This deflection can be measured by measuring the position of the light beam on the position detector 14. The information produced during the measurement of the concentration gradient relates to the universal property of the solute—refractive index n. Consequently, the concentration gradient produced by any solute that has a different n than the solvent will be detected by noting a deflection or tilt in the light beam. Similarly, if a temperature difference exists in the medium in the sample chamber, a temperature gradient exists which forms the corresponding refractive index gradient dn/dx=(dn/dT)(dT/dx). This will also tilt or deflect the propagating light beam by an angle $\theta = (D/n)(dn/dT)(dT/dx)$.

Figure 3:
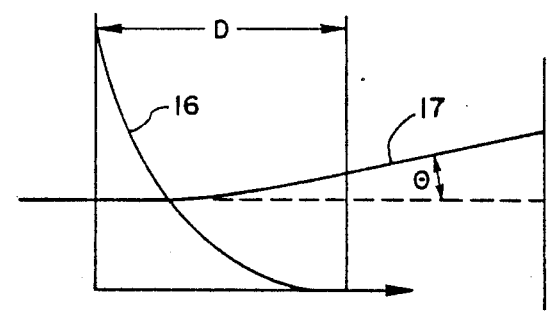
Figure 4:
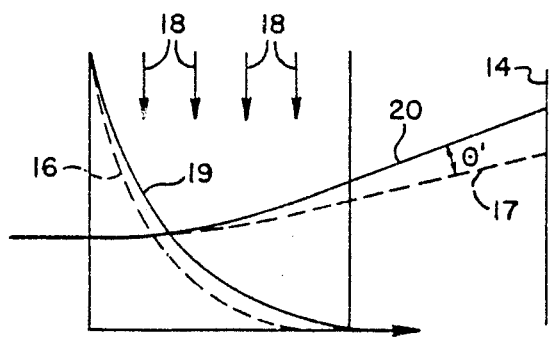

FIG. 3 shows the same principal as FIG. 2, but illustrates it somewhat differently. Thus, if a concentration gradient represented by line 16 exists in a sample in a sample chamber defined by walls 12 and 13, a probe beam of light 17 directed through the sample will be deflected as indicated above by an angle $\theta$. This causes the position of the beam to move on the surface of the position sensor 14 as indicated above.

Where a concentration gradient exists in a sample and the sample is irradiated with energy that is absorbed by one of the components forming the concentration gradient, it has been found that a temperature gradient is also formed. If the sample is uniformly irradiated, the temperature gradient formed will correspond to the concentration gradient of the absorbing component. This is illustrated by FIG. 4 where the sample is irradiated by an excitation beam indicated by arrows 18 which may be a light beam of wavelength which is absorbed by the component of the sample producing the concentration gradient 16. If the excitation beam is supplied periodically, the absorbing component will absorb the energy relaxing the energy to the medium around it causing heating when being irradiated, i.e. when the excitation beam is on, and when the excitation beam is off, the heat generated will be disipated into the medium. Since the absorbtion of energy in the sample will be by the absorbing component, the amount of energy absorbed will be in proportion to the concentration of the absorbing component of the sample and the temperature gradient produced will correspond to the concentration gradient. The temperature gradient produced is represented by line 19 in FIG. 4. The temperature gradient produces refractive index gradient and causes a further deflection of the probe beam as shown for beam 20 in FIG. 4 which is deflected from beam 17 shown in broken lines in FIG. 4 which represents the deflected beam caused by merely the concentration gradient. The increased deflection is indicated by $\theta'$ and can be determined by measuring the position of beam 20 on position sensor 14.

From the mathematical standpoint, as was mentioned above, a probe light beam passing through the concentration gradient that is present in the sample will undergo deflection $$\theta = (D/n)(dn/dc)dc/dx$$

If an additional temperature gradient is produced by the excitation beam absorbed by the component forming the concentration gradient and is assumed to be uniform, the temperature gradient profile corresponds to the concentration gradient profile. For example, when a pulsed excitation beam of intensity $I_o$ (J/cm$^2$ per pulse) is used then $$dT/dx = Z(I_o/C_h\cdot\rho)2.303\epsilon\lambda(dc/dx)$$

where Z is a coefficient describing the fraction of absorbed energy converted to heat, $C_h$ is the specific heat of the medium in J/(g·deg), $\rho$ is the density of the medium in g/cm$^3$, and $\epsilon\lambda$ is the molar absorptivity in L/(cm·mol). This temperature gradient will form the periodic refractive index gradient dn/dx which will deflect the probe beam by $\theta'$, with $$\theta' = (D/n)(dn/dT)Z(I_o/C_h\rho)\epsilon\lambda(dc/dx)$$

The modulated deflection signal $\theta'$, corresponding to pulsing frequency, is expected to increase proportionally with molar absorptivity and the concentration gradient magnitude. In the above formula we assumed uniform irradiation of the concentration gradient by the pulsed light source. Therefore no significant light intensity gradient in the deflection direction can exist in the medium. This condition will hold for low concentrations of the absorbing species and/or appropriate geometry of the experimental arrangement.

Figure 5:
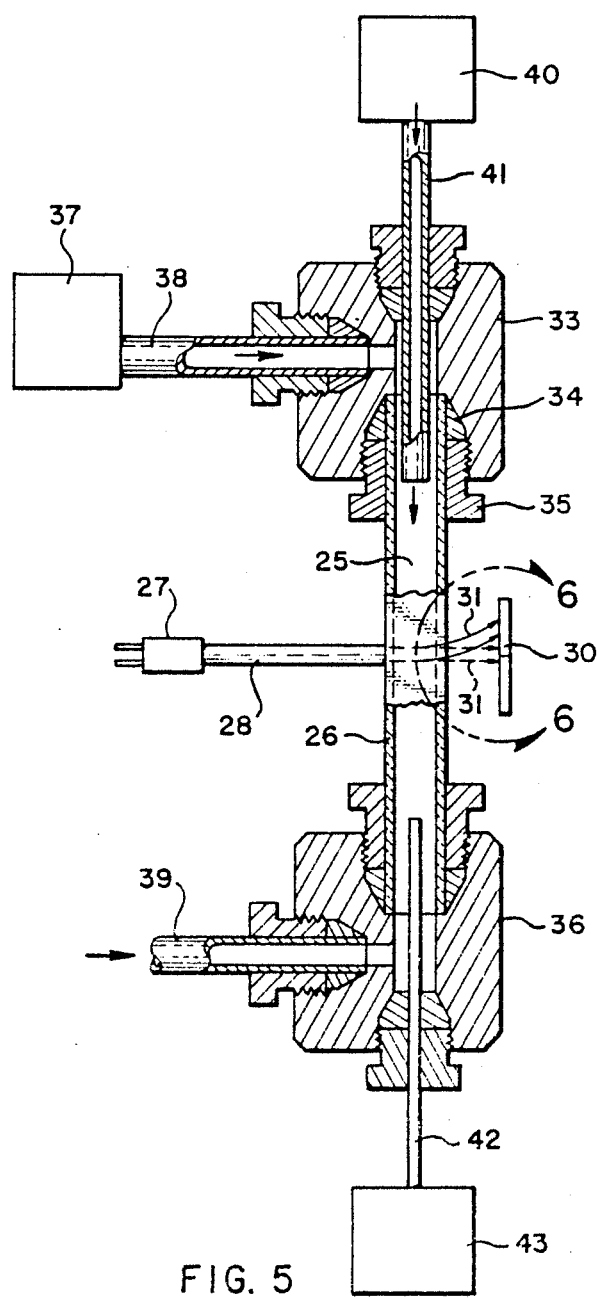
Figure 6:
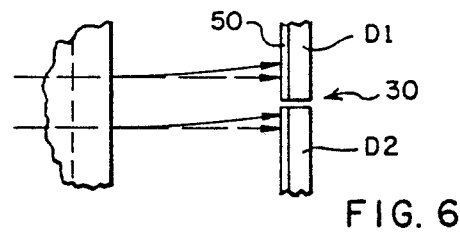

FIG. 5 shows a detector of the invention. A sample chamber 25 is formed from a piece of square capillary tube 26 having transparent sides such as manufactured by Wale Aparatus Co., of Hellertown, Pa. The inside dimensions between walls can vary, with dimensions between 1 and 0.2 mm having been found satisfactory. A light emitting diode (LED) 27 coupled to a multimode optical fiber 28 as by gluing is positioned so that the light beam transferred through the optical fiber, the probe light beam, enters the sample chamber 25 in a direction transverse to the sides of tube 26. A combination LED-optical fiber unit is available from Laser Diode Laboratories, Inc., New Brunswick, N.J., as model IRE 160FB. The LED is connected to a source of power, not shown, to cause it to illuminate. A position detector 30 is positioned on the opposite side of the sample chamber so as to measure the deflection of the probe light beam passing through the sample chamber. It is preferred that the detector 30 be positioned so that a probe light beam 31 passing directly through the sample chamber as shown by the broken lines falls directly on the center of the detector. The probe light beam will pass directly through the sample chamber when no sample is in the chamber or when a sample in the chamber does not generate a refractive index gradient of any kind. As a gradient moves through the chamber in front of the probe light beam, the beam is deflected as shown in solid lines and falls on a different portion of detector 30. The bending shown in FIG. 5 is exagerated for purposes of illustration as in practice the deflection of the beam generally will be small. FIG. 6 shows an enlargement of the position detector with a smaller movement of the probe light beam.

Tube 26 is secured to a standard T connection 33, as used in chromatography and as made by Valco Instruments Co., of Houston, Tex. These T's are made for round tubing so special packing 34 must be made to seal tube 26 to T 33. The tube 26 and packing 34 are held in position by threaded ferrule 35. A similar T 36 is secured in similar manner to the other end of tube 26. A source of solvent 37 is connected by tube 38 to T 33 in normal manner so that solvent can flow from source 37 into T 33 and then through tube 26 forming sample chamber 25. The solvent then flows into T 36 and out through tube 39 secured to T 36. A source of sample fluid 40 such as an open tubular capillary liquid chromatographic column equipped with an injector has a capillary tube 41 extending therefrom through T 33 and into sample chamber 25 in tube 26. Water may be used with such column as the mobile phase. In such case, the sample eluting from the column consists of a stream of water in which various of the separated components to be determined, as separated by the column, are spaced. Thus, concentration gradients exist in the sample as the sample stream changes from pure water to each component solution and back again. The sample enters the sample chamber from tube 41 and enters the center of the solvent stream flowing through sample chamber 25 from T 33 around tube 41. The solvent provides a sheath flow for the sample from tube 41. The sheath flow keeps the sample from fully expanding to fill the volume of the sample chamber but allows some expansion of the sample in the solvent to improve sensitivity of detection. Further, the sheath flow keeps the samples from the walls of the sample chamber where components thereof might be absorbed into the walls and interfere with further operation of the detector. This is a particular consideration if a fluorescence detector is to be used in the sample chamber to provide an fluorescence measurement in addition to the beam deflection measurement. In such case, the fluorescence detector is operated in normal fashion in addition to the operation of the invention as described. Where water is used as the mobile phase for the separation, water will be used as the solvent so that a concentration gradient is not formed between the mobile phase and the solvent. After flowing through the sample chamber, the sample and solvent flow into tubing 39 and is directed to waste or storage or further evaluation as desired.

Figure 7:
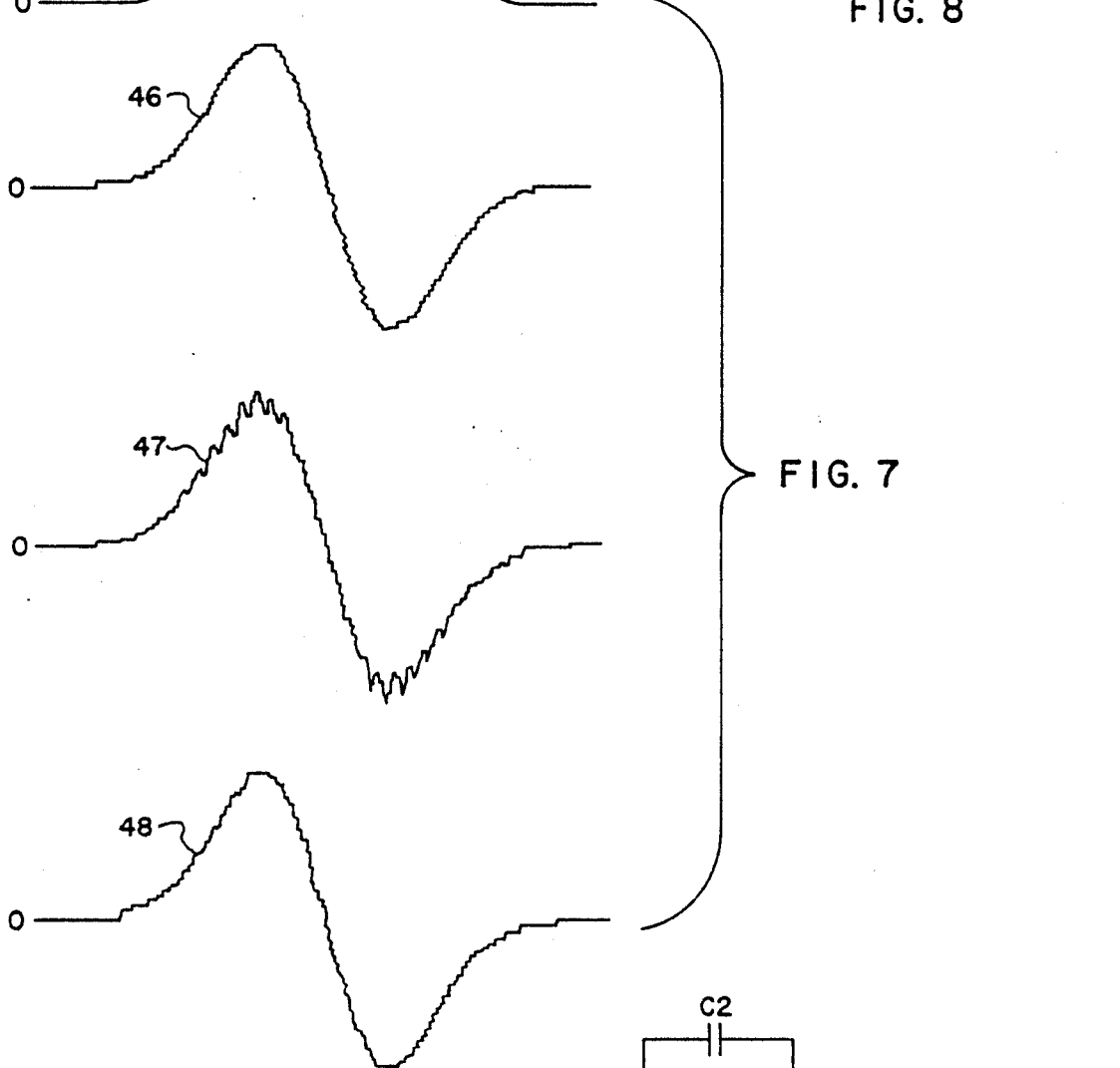

The concentration profile of a particular component in the sample stream will theoretically have a Gaussian shape as shown by curve 45 in FIG. 7. This is because some dispersion of the component in the water carrying it will occur. In practice, the concentration profile is usually close to a Gaussian shape. The 0 axis for curve 45 represents the carrier or solvent. The concentration of a component will increase rapidly to a peak value and then decrease rapidly back to the solvent. The height of the peak will depend upon the amount of the component present.

A concentration gradient is present in the sample as the concentration of a component increases. This causes the probe light beam to be deflected as shown in Curve 46. As the concentration gradient passes its inflection point, the deflection of the beam reaches a peak. From the inflection point, the concentration gradient decreases as the concentration itself continues to increase. Thus, the deflection of the probe beam decreases. As the concentration reaches a peak, the beam deflection becomes zero as shown by the zero crossover of curve 46. As the concentration drops, a concentration gradient again exists and the beam is deflected in the opposite direction causing the negative peak of curve 46 and then moves back to zero deflection as the concentration change decrease and becomes only solvent again. It will be recognized that curve 46 generated by measuring the concentration gradient is substantially a first differential of the concentration profile 45.

A separate curve 46 will be generated for each Gaussian peak gradient passing through the sample chamber. If a chromatographic column is supplying the sample, identification of the particular components from the column are generally determined by their retention times which are indicated by their location in the stream. Thus, retention time is determined by when the curve 46 occurs after the sample starts flowing through the sample chamber. Positive identification of a component is often difficult, however, where concentration peaks overlap, or where the actual concentration of a component is small so it is difficult to determine if a peak has actually been detected.

It has been found that positive identification in such instance can be made using the detector of the invention by introducing energy on a periodic or pulsed basis into the sample chamber in a form which is selectively absorbed by a predetermined possible component. Thus, in the detector of FIG. 5, an optical fiber 42 coupled to a light source 43 extends through T 36 and has its end positioned to direct excitation light exiting therefrom into the detection zone of the sample chamber. Such excitation light should be directed substantially evenly over the entire sample within probe light beam 31. The wavelength of the excitation light is selected so that it is absorbed by a particular possible component to be detected, but not absorbed by other components of the sample. The excitation light is then chopped, pulsed, or otherwise periodically directed into the sample in the detection zone. If the predetermined component to be measured is present, it will absorb the energy from the excitation light during the time such light is on. This causes a temperature gradient to be formed in the sample as explained above. This temperature gradient will be detected by the light beam 21 and superimpose a periodic signal corresponding to modulation or pulsing frequency onto curve 46 with each pulse thereby creating a curve 47 with superimposed pulses. This gives positive identification of the component exhibiting curve 47.

It has been found that the excitation light beam may be provided periodically by use of a chopper in light source 43. The chopper may be a set of blades which pass between the actual light source and the optical fiber 42 to produce equal periods of on and off light of a fixed frequency. If the output signal of the detector is passed through a lock-in amplifier, which is an amplifier which will only amplify signals of a predetermined frequency and phase, and the frequency for amplification is set for the frequency of the chopping of the excitation beam, the curve 47 of FIG. 5 will be amplified to form curve 48. An example of a lock in amplifier satisfactory for use with the invention is a Model 5208 manufactured by Princeton Applied Research of Princeton, N.J. Curve 46, which does not have the temperature gradient deflection superimposed thereon will not produce any curve through the lock in amplifier. If the excitation beam is pulsed rather than chopped, a gated amplifier may be used to amplify the output signal only during the on time of the excitation beam or slightly longer. Such gated amplification will also result in output curve 48. The existance of output curve 48 provides positive identification of the presence of the substance which absorbs the excitation beam.

An example of the identification method described above is the identification of an amino acid derivatized with dansyl chloride during the separation of derivatized amino acids. Such derivatized amino acids absorbs light of a wavelength in a range around 360 nanometers. The excitation beam may be formed by a light source such as a helium-cadnium laser which produces light of 325 nanometers which will be absorbed by the dansyl chloride, or a xenon lamp with a monochometer to produce light of 360 nanometers. With such excitation beam, a curve similar to 47 will be produced by the position detector when the amino acid derivatized with dansyl chloride passes through the detector and processing such signal with a lock in amplifier will produce a curve similar to 48. Other underivatized chemical compounds present in the stream will be detected through the concentration gradient, but will not produce the curves of 47 and 48.

FIG. 14 is a block diagram showing how the signals 46, 47, and 48 are generated. Signals 46 and 47 are generated by the position detector. Such signals will generally be amplified by amplifier before being observed or stored for later evaluation. Thus, the output of the amplifier will give curves 46 and 47. As indicated above, if the output of the amplifier is processed such as by feeding it through a lock in amplifier or gated amplifier as described, signal 48 results.

As indicated, it is preferred that the probe light beam be generated by an LED. It has been found that light from an LED is more positionally and intensity stable than light from a laser and as a result, the detector is much more sensitive when using LED probe light than when using a laser. Further, the preferred LED light is in the near infrared or infrared range and is more compatible with silicon light detectors used for the position sensors and is less likely to be of a wavelength to be absorbed by chemical compounds which are components of a sample to be detected.

Figure 8:
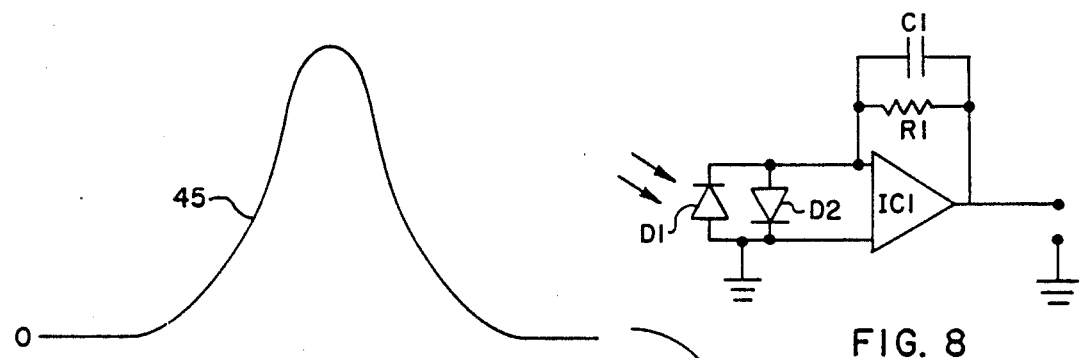

While any position sensor can be used to measure the movement of the probe light beam, such as PIN-SPOT/2D silicon detector with a Model 301 DIV signal conditioning amplifier as manufactured by United Detector Technology of Hawthorne, Calif., specific simple position detection circuitry found satisfactory for use with the present invention in a detector such as shown in FIGS. 5 and 6 is shown in FIG. 8. The position sensor 31, FIG. 6, is made up of two photo diodes D1 and D2, FIG. 8, such as S1087-01 or S2506 manufactured by Hamamatsu Corporation, Bridgewater, N.J. The cases of these diodes will preferably be shaved where appropriate so that the light sensitive surfaces can be located close together. These diodes are connected in parallel with opposite orientations, as shown, and the parallel combination is connected to the inputs of an operational amplifier IC1 such as an OPA-111 manufactured by Burr Brown of Tuscon, Ariz. The gain of the amplifier is set in normal fashion by feedback resistor R1 and the bandwidth of the amplifier is set by capacitor C1.

With the probe beam centered on the detector as shown in broken lines in FIG. 6, light falls equally on diodes D1 and D2 and no output is produced by amplifier IC1. If the probe light moves, it will illuminate one diode more than the other. In this instance, the more highly illuminated diode will produce a higher current output than the less illuminated diode. The current on the input to IC1 will thus be unequal and an output proportional to the differences of the inputs will be produced. The output of IC1 may be viewed in real time and will preferably be recorded for later study by any convenient means such as a chart recorder or a computer. The output of IC1 corresponds to the output of the amplifier in FIG. 14 and produces the curves 46 and 47. It has been found that this detector works well to sensor position changes of the probe beam. In practice, a filter 50 may be placed in front of detector 31 to filter out background room light and the excitation light thus limiting the light reaching the filter to only that of the probe beam.

While an example of a sample source has been given as a capillary chromatographic column, various sample sources are available. Any sample which provides concentration gradients can be used. Further, if a homogenious sample is to be evaluated by using the detector, small amounts or plugs of the sample may be introduced periodically through tube 41 into the solvent flowing through the sample to provide concentration gradients between the solvent and the sample plugs which can be detected and evaluated using the detector of the invention.

FIG. 9 shows the detector of the invention set up for use as a capillary zone electrophoresis detection device. A square capillary tube 51 is secured between standard T's 52 and 53 in normal manner as described above to form sample chamber 54. Here, however, tube 51 extends into T 52 a sufficient distance so that end 51a extends into the flow path 55 through T 52. One end of flow path 55 is connected through tubing 56 to a valve 57 which is connected through tubing 58 to a source of solvent 59 and through tubing 60 to a sample source 61. The solvent and sample are generally supplied to tubings 60 and 61 under pressure such as by pumps in the solvent and sample sources. The other end of flow path 55 is connected to tubing 62 which extends to waste or other desired storage. Tube 51 forming sample chamber 54 is connected through T 53 to tubing 63 which again leads to waste or desired storage.

An optical fiber 64 extends from a source of excitation light 65, through T 53 into sample chamber 54. An LED 66 coupled to optical fiber 67 produces a probe beam of light which is directed through tube 51 and sample chamber 54 to beam position detector 68. Operation of the probe beam and position detector are as described above in relation to FIG. 5. In the embodiment of FIG. 9, T 52 and T 53 are electrically connected, such as by wires 69, to opposite sides of a source of electrical potential such as a high voltage D.C. power supply 70 indicated in FIG. 9 as a battery. T 52 and T 53 are made of stainless steel and act as electrodes. With voltage supply 70 connected as shown, an electrical potential gradient is established in the solvent in the sample chamber 54. In operation, solvent flows through flow passage 55 with some of the solvent being drawn into and flowing through sample chamber 54 by reason of the electrical potential gradient or by pressure produced in flow 55. Periodically, valve 57 is operated to inject sample into tube 56 and flow passage 55. As the sample passes the end of capillary tube 51, a portion of the sample is drawn into and through sample chamber 54. The electrical potential in the system causes flow through the sample chamber and also causes separation of the components of the sample as it flows into the sample chamber due to different charges of the molecules and their mobilities. Such separation sets up concentration gradients which are detected and measured as indicated for FIG. 5. If specific identification of a component of the sample is desired, an excitation beam is provided by light source 65 through optical fiber 64.

A further embodiment of a detector of the invention is shown in FIG. 10, wherein the detector is made by using a standard cross connector 75 as also manufactured by Valco Instruments Co., Inc. A sample supply tube 76 is attached to one side of the cross while a sample discharge tube 77 is connected to the opposite side of cross. The sample thus flows through passage 78 in the cross. An optical fiber 79 within tubing 80 extends into a side of the cross transverse to the flow of sample and is sealed in place in tubing 80 by suitable plug material 81. An LED 82 is coupled to the end of optical fiber 79 to produce the probe beam. Optical fiber 83 positioned in tubing 84 extends into the opposite end of cross 75 and is connected to a light detector 85. It will be noted that optical fiber 79 from which the probe beam originates is a smaller diameter than optical fiber 83 which receives the probe beam after passage through the sample. For example, fiber 79 may have a diameter of fifty micrometers while fiber 83 has a diameter of two hundred micrometers. The fiber 79 is positioned with respect to fiber 83 so that with a nondeflected probe light beam, only a portion (about 50 percent) of the probe light beam enters fiber 83. Then, as the beam is deflected, either more or less of the probe beam enters fiber 83 depending upon the direction of deflection of the beam.

Figure 11:
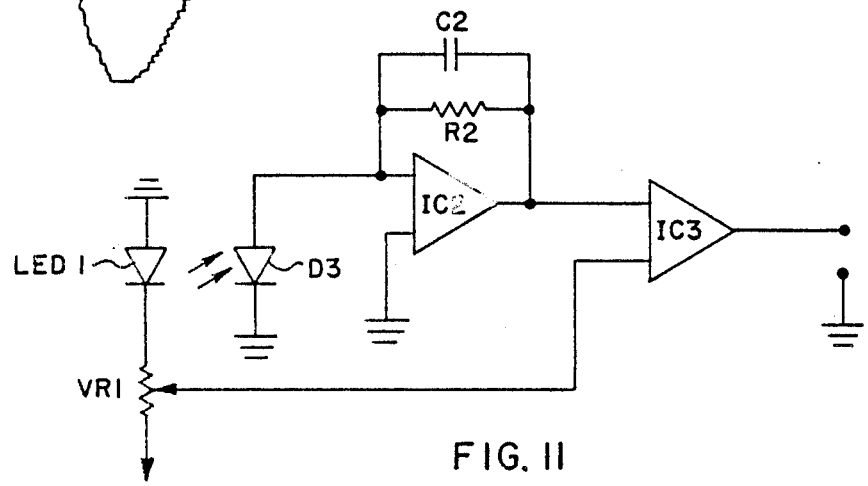

With this arrangement, a single light sensor can be used since the intensity of the light collected by optical fiber 83 is an indication of the deflection of the beam. A light sensor suitable for use in this embodiment of the invention is shown in FIG. 11. LED1 is the LED generating the probe light beam. Photodiode D3 is detector 85. The output of diode D3 is connected to the inverting input of operational amplifier IC2 which may be an OPA111 manufactured by Burr Brown. The noninverting input of IC2 is connected to ground. The gain of IC2 is determined by the value of feedback resistor R2 and the bandwidth of the amplifier is determined by capacitor C2. The output of IC2 is an amplified signal proportional to the output of D3 which is proportional to the light entering fiber 83. The output of IC2 is connected to an input of differential amplifier IC3 which may be an OPA101 manufactured by Burr Brown. The other input to IC3 is connected to variable resistor VR1 which serves as a current limiting resistor for LED1 and also as a voltage divider for the input of IC3. VR1 will be adjusted so that with no deflection of the probe light beam, the output of IC3 will be zero. The output of IC3 will then be proportional to the deflection of the probe beam for small deflections. By typing an input of IC3 to VR1, any change in current through LED1 which would change its intensity is compensated for by the change in voltage on VR1 and the voltage supplied to the input of IC3 by VR1. The output of IC3 corresponds to the amplifier output in FIG. 14.

In some instances where a concentration of a compound existing in a sample is too small to be detected by the normal detection means of merely passing the sample through a probe light beam in a sample chamber, or with a homogeneous sample, a concentration gradient can be enhanced or created by means of electrochemistry. In these cases an electrode is placed in the sample chamber as shown in FIG. 12. The sample chamber 90 may be formed by square tube 91 as for the detector of FIG. 5 and the sample may be supplied in manner as shown in FIG. 5. A platinum electrode 92 is positioned within the sample chamber as shown. The probe light beam 93 in this case is generated by a laser 94 so that it is highly columnated and is focused by lens 95 at a position directly above the active electrode surface 96 of electrode 92. The highly columnated, focused beam is necessary because it has to accurately pass a known distance from the electrode surface, which distance is preferably several microns from the electrode surface and generally no more that 100 microns from the surface.

With a potential applied to the surface 96 of electrode 92, certain components of a sample will be chemically reduced or oxidized by the addition substraction of one or more electrons to form a product. The product has a high concentration next to the electrode surface and the concentration rapidly drops to zero within the diffusion layer (usually about 100 microns) above the electrode surface. While the product has high concentration next to the electrode surface, the component which is reacted (oxidized or reduced) will have a very low concentration next to the electrode surface. Thus, the electrode generates concentration gradients immediately adjacent its surface of reactant and product. The concentration gradient of reactant formed above the electrode is mathematically expressed as:

$$dc_A/dx(x_o, t_o) = ((exp(x_o^2/4D_o t_o))/((\pi D_o t_o)^{\frac{1}{2}}))C_o$$

Where $dc_A/dx$ is the concentration gradient at a distance $x_o$ from the surface of the electrode at a time $t_o$ after applying the potential to the electrode, $C_o$ is the concentration of the reactant in the sample, and $D_o$ is the diffusion coefficient of the reactant in the medium. It should be noted that the magnitude of the concentration gradient at fixed distance from the electrode is proportional to the concentration of the reactant in the sample. The proportionality constant is very large or small $t_o$ and $x_o$. This concentration gradient can be detected by measuring the deflection of the probe light beam as explained above. Since usually there will be opposing concentration gradients formed, an excitation beam of light can be directed on the electrode surface by optical fibers 97 so that one of the gradients is selected for detection through creation of a temperature gradient as explained above. This method will substantially increase sensitivity and selectivity of the measurement.

While the excitation beam in the various examples has been described as a light beam of selected wavelength, other excitation energy beams may be used such as microwaves which can selectively input energy and thus heat selected components of a sample.

Due to the simplicity of the detectors, a detector of the invention can be made with vary small sample chamber volumes and by using sheath flow can accomodate sample volumes even smaller than the sample chamber volume. Sample chambers having cross sectional areas down to four nanometers have been successfully tested. Also, use of silicon devices such as LED's and silicon light detectors indicate that a detector of the invention might be integrated on a single chip.

In addition to merely indicating the presence and extent of a concentration gradient, the data obtained by way of curves 46 and 48 can also be used to determine the actual concentration of the detected chemical compounds in the sample, the value of the positive peak of curve 46 or curve 48 or the negative peak (the negative peak in practice is generally less than the positive peak) are both proportional to the actual concentration. By experimentally establishing the proportionality constant in a manner well known for establishing such constant for use with detectors which produce a concentration curve similar to curve 45, the actual concentration of a chemical compound detected as present in a sample can be easily determined.

So far, we have discussed detecting a concentration gradient or superimposed temperature gradient by measuring the amount of deflection of a probe light beam caused by the gradient. The amount of deflection measured supplies information about the gradient, the compound creating the gradient and the concentration of the compound in the sample. Rather than measuring the deflection produced by a given unknown gradient, a known refractive index gradient produced by a concentration gradient can be created in a material which is then passed through a probe light beam or positioned in a probe light beam to create a known predetermined deflection of the beam. For example, as shown in FIG. 13, an LED 100 coupled to an optical fiber 101 creates a probe beam of light directed through a movable or fixed medium 102 such as a solid plastic material. This material is treated to create known concentration gradients at known positions. The concentration gradients are also created in such a way that they absorb one or more excitation wavelengths. In this way, the positioning of the probe beam can be controlled. For example, with medium 102 positioned so the probe does not pass through a gradient, the beam will hit detector 103 and cause an output therefrom. If medium 102 is positioned so that the probe beam passes through the concentration gradient, the beam is deflected to sensor 104 and causes an output therefrom. While the beam is passing through the gradient, if an excitation beam is provided to the gradient as by a light beam of specific bandwidth from optical fiber 105, the probe light beam is deflected to sensor 106. Other excitation beams could cause additional different movement of the light beam. Such a system of controlling the deflection of a light beam in a known manner could be used in a number of ways, for example, to store information through the creation of known gradients and then process the information in various ways as the information is read back.

Whereas this invention is here illustrated and described with specific reference to an embodiment thereof presently contemplated as the best mode of carrying out such invention in actual practice, it is to be understood that various changes may be made in adapting the invention to different embodiments without departing from the broader inventive concepts disclosed herein and comprehended by the claims that follow.

I claim:

1. A method of identifying and measuring a concentration gradient of a known compound above a surface which forms a concentration gradient extending in a concentration gradient direction thereabove, comprising the steps of passing a probe beam of light through the concentration gradient a known distance above the surface; selecting an excitation energy that will be absorbed by the known compound; supplying the excitation energy substantially uniformly in the concentration gradient direction through at least the portion of the area above the surface through which the probe beam passes so that the excitation energy will be absorbed by the known compound in the concentration gradient thereby causing the creation of a temperature gradient above the surface which is proportional to the concentration gradient of the known compound above the surface; and measuring the deflection of the probe beam of light passing through the concentration gradient and temperature gradient above the surface caused by the presence of the concentration gradient and temperature gradient above the surface.

2. A detector for detecting a concentration gradient of a known compound above a surface which forms a concentration gradient extending in a concentration gradient direction thereabove, comprising a surface; means for creating a concentration gradient of a known compound above said surface; means for passing a probe beam of light a known distance above the surface and through the concentration gradient formed thereabove; means for detecting the position in the concentration gradient direction of the probe beam of light after passing above the surface; and means for periodically supplying excitation energy uniformly in the concentration gradient direction through the area above the surface through which the probe beam passes, said energy adapted to be absorbed by the known compound forming the concentration gradient above the surface to thereby create a temperature gradient above the surface proportional to the concentration gradient which will cause deflection of the probe beam in addition to any deflection caused by the concentration gradient above the surface.

3. A detector according to claim 2, wherein the excitation energy is light of a predetermined wavelength and is supplied periodically to the concentration gradient through which the probe beam passes by directing a beam of such light periodically onto such gradient.

4. A detector according to claim 3, wherein the beam of excitation light is supplied periodically by chopping the beam at a known frequency.

5. A detector according to claim 4, wherein the means for determining the position of the probe beam after passing through the concentration gradient produces an output signal indicative of the position of the beam and wherein said output signal is processed to separate any component of the signal representing position of the beam that may be due to absorption of the excitation energy from the components of the signal representing position of the beam due to the concentration gradient.

6. A detector according to claim 5, wherein the output is processed by an amplifier which amplifies only signals of the same frequency as the frequency of the chopping of the excitation beam.

7. A detector according to claim 3, wherein pulses of excitation light are supplied to the concentration gradient through which the probe beam passes.

8. A detector according to claim 7, wherein the means for determining the position of the probe beam after passing through the concentration gradient produces an output signal indicative of the position of the beam and wherein said output signal is processed to separate any component of the signal representing position of the beam that may be due to absorption of the excitation energy from the component of the signal representing position of the beam due to the concentration gradient.

9. A detector according to claim 8, wherein the output is processed by an amplifier which amplifies only signals sensed close to the pulses of excitation light.

10. A detector according to claim 2, wherein the means for determining the position of the probe beam after passing through the concentration gradient produces an output signal indicative of the position of the beam and wherein said output signal is processed to separate any component of the signal representing position of the beam that may be due to absorption of the excitation energy from the component of the signal representing position of the beam due to the concentration gradient.

11. A method of controlling and varying the position of a light beam after passing through a positioning medium, comprising the steps of generating a light beam to be controlled; passing the light beam through a positioning medium; creating a concentration gradient in the positioning medium in the path of the light beam which changes the refractive index of the positioning medium when it is desired to vary the position of the light beam; and supplying excitation energy to the concentration gradient to form a temperature gradient in addition to the concentration gradient to thereby further change the refractive index of the positioning medium when it is desired to further vary the position of the light beam.

12. A method of controlling and varying the position of a light beam according to claim 11, wherein the step of supplying excitation energy to the concentration gradient includes the step of directing light of a predetermined wavelength to the concentration gradient to be absorbed by one of the components of the concentration gradient to thereby produce the temperature gradient.

13. A method of controlling and varying the position of a light beam, comprising the steps of generating a light beam to be controlled; placing a concentration gradient in the path of the light beam so that the light beam passes therethrough and is deflected by a refractive index gradient formed by the concentration gradient; supplying excitation energy to the concentration gradient to form a temperature gradient in addition to the concentration gradient to thereby vary the refractive index gradient through which the light beam passes when it is desired to vary the position of the light beam, the change in refractive index gradient causing a change in the deflection of the light beam passing through the refractive index gradient to thereby vary the position of the light beam.

14. Apparatus for controlling and varying the position of a light beam after passing through a positioning medium, comprising means for generating a light beam to be controlled; a positioning medium in the path of the light beam so the light beam passes therethrough; means for generating a concentration gradient in the positioning medium through which the light beam passes to change the refractive index of the positioning medium when it is desired to vary the position of the light beam; and means for supplying excitation energy to the concentration gradient through which the light beam passes, said energy adapted to be absorbed by a component of the concentration gradient to thereby create a temperature gradient proportional to the concentration gradient which will further change the refractive index of the positioning medium, when it is desired to further vary the position of the light beam.

15. Apparatus for controlling and varying the position of a light beam according to claim 14, wherein the excitation energy is light of a predetermined wavelength and wherein the means for supplying excitation energy includes means for directing a beam of said light of a predetermined wavelength onto the concentration gradient in the positioning medium through which the light beam passes.

* * * * *